US005734029A

United States Patent [19]
Wulff et al.

[11] Patent Number: 5,734,029
[45] Date of Patent: Mar. 31, 1998

[54] PREPARATION OF IMPROVED ALKYPOLYGLOYCOSIDE SURFACTANT MIXTURES

[75] Inventors: Harald P. Wulff, Bryn Mawr; Paul A. Siracusa, Perkasie, both of Pa.; Patricia E. Bator, Secaucus; Barry A. Salka, Fair Lawn, both of N.J.; Michael W. Counts, Ambler; Robert A. Aleksejczyk, Hatfield, both of Pa.

[73] Assignee: Henkel Corporation, Plymouth Meeting, Pa.

[21] Appl. No.: 475,474

[22] Filed: Jun. 7, 1995

Related U.S. Application Data

[63] Continuation of Ser. No. 876,967, Apr. 30, 1992, abandoned, which is a continuation-in-part of Ser. No. 744,430, Oct. 10, 1991, abandoned.

[51] Int. Cl.$^6$ .......................... C07G 3/00; A01N 43/04; A61K 31/70; C11D 1/00
[52] U.S. Cl. .......................... 536/4.1; 536/18.6; 536/124; 536/120; 514/23; 514/25; 252/174.17
[58] Field of Search ................... 536/18.6, 4.1, 536/124, 127, 120; 514/23, 25; 252/174.17

[56] References Cited

U.S. PATENT DOCUMENTS

| | | | |
|---|---|---|---|
| 3,219,656 | 11/1965 | Boettner | 536/18.3 |
| 3,547,828 | 12/1970 | Mansfield et al. | 252/351 |
| 3,598,865 | 8/1971 | Lew | 536/18.6 |
| 3,707,535 | 12/1972 | Lew | 536/18.6 |
| 3,772,269 | 11/1973 | Lew | 536/18.6 |
| 3,839,318 | 10/1974 | Mansfield | 536/18.6 |
| 3,886,277 | 5/1975 | Randebrock et al. | 424/258 |
| 4,154,706 | 5/1979 | Kenkare et al. | 252/547 |
| 4,196,201 | 4/1980 | Boelle et al. | 424/180 |
| 4,304,679 | 12/1981 | Hooper et al. | 252/106 |
| 4,323,468 | 4/1982 | Grollier et al. | 252/174.17 |
| 4,349,669 | 9/1982 | Klahr et al. | 536/127 |

(List continued on next page.)

FOREIGN PATENT DOCUMENTS

| | | |
|---|---|---|
| 0092355 | 10/1983 | European Pat. Off. . |
| 0096917 | 12/1983 | European Pat. Off. . |
| 0132043 | 1/1985 | European Pat. Off. . |
| 0185971 | 7/1986 | European Pat. Off. . |
| 0444262 | 9/1991 | European Pat. Off. . |
| 2017240 | 5/1970 | France . |
| 3316250 | 11/1984 | Germany . |
| 63-298821 | 11/1988 | Japan . |
| 8801639 | 3/1988 | WIPO . |

OTHER PUBLICATIONS

DataBase WPIL, Derwent Publications Ltd., London, GB, AN 90-2144522 & JP,A, 2 145 696 (Nippon Corn Starch) 5 Jun. 1990.

"Preparation and Properties of Pure Alkyl Glucosides, Maltoside and Maltotrisides", JAOCS, vol. 61, No. 10, pp. 1651–1655, Oct. 1984; Physical and Functional Properties of Some Higher Alkyl Polyglucosides, JAOCS, vol. 47, pp. 162–167, 1970.

*Primary Examiner*—John Kight
*Assistant Examiner*—Everett White
*Attorney, Agent, or Firm*—Ernest G. Szoke; Wayne C. Jaeschke; Patrick J. Span

[57] ABSTRACT

An improved alkylpolyglycoside surfactant composition, and method of preparing same, by selecting an average chain length of the alkyl moiety of the composition and mixing two or more of at least binary components having an average alkyl chain lengths such that when mixed, the amounts thereof are effective to provide the predetermined, selected average alkyl moiety of the surfactant composition. The improved alkylpolyglycoside composition is used in a variety of end-use applications, including hard surface cleaners, laundry detergents, and personal care products, such as shampoos, soaps, facial cleansers, foam baths, toothpaste, mouthwashes, antiperspirants and the like.

70 Claims, 1 Drawing Sheet

U.S. PATENT DOCUMENTS

| | | | |
|---|---|---|---|
| 4,393,203 | 7/1983 | Mao et al. | 536/124 |
| 4,396,520 | 8/1983 | Payne et al. | 252/89.1 |
| 4,472,170 | 9/1984 | Hellyer | 536/18.6 |
| 4,483,779 | 11/1984 | Llenado et al. | 252/135 |
| 4,483,780 | 11/1984 | Llenado | 252/135 |
| 4,493,773 | 1/1985 | Cook et al. | 252/8.8 |
| 4,510,306 | 4/1985 | Langdon | 536/127 |
| 4,536,318 | 8/1985 | Cook et al. | 252/174.17 |
| 4,536,319 | 8/1985 | Payne | 252/174.17 |
| 4,565,647 | 1/1986 | Llenado | 252/354 |
| 4,597,770 | 7/1986 | Forand et al. | 536/18.6 |
| 4,599,188 | 7/1986 | Llenado | 252/174.17 |
| 4,606,850 | 8/1986 | Malik | 252/528 |
| 4,627,931 | 12/1986 | Malik | 252/153 |
| 4,657,999 | 4/1987 | Hoefer et al. | 526/200 |
| 4,663,069 | 5/1987 | Llenado | 252/117 |
| 4,668,422 | 5/1987 | Malik et al. | 252/174.17 |
| 4,678,595 | 7/1987 | Malik et al. | 252/174.17 |
| 4,704,453 | 11/1987 | Lorenz et al. | 536/18.6 |
| 4,705,665 | 11/1987 | Malik | 422/12 |
| 4,713,447 | 12/1987 | Letton | 536/18.6 |
| 4,732,696 | 3/1988 | Urfer | 252/174.17 |
| 4,732,704 | 3/1988 | Biermann et al. | 252/548 |
| 4,748,158 | 5/1988 | Biermann et al. | 514/25 |
| 4,767,559 | 8/1988 | Kruse et al. | 252/106 |
| 4,780,234 | 10/1988 | Malik et al. | 252/135 |
| 4,900,721 | 2/1990 | Bansemir et al. | 514/25 |
| 4,987,225 | 1/1991 | Pickens | 536/124 |

FIG. 1

PREPARATION OF IMPROVED ALKYPOLYGLOYCOSIDE SURFACTANT MIXTURES

This application is a continuation of application Ser. No. 07/876,967 filed on Apr. 30, 1992 (now abandoned), which is a continuation-in-part of Ser. No. 07/774,430 filed on Oct. 10, 1991 (now abandoned).

BACKGROUND OF THE INVENTION

1. Field of the Invention

This invention relates to the preparation of novel alkylpolyglycoside compositions having unexpectedly enhanced surfactant properties from readily available mixtures of alkylpolyglycosides of differing alkyl chain lengths, varying degrees of polymerization (DP) and surfactant properties. This invention further relates to the preparation of novel, economical and environmentally friendly mixtures of alkylpolyglycosides of preselected average alkyl chain length for a wide variety of surfactant uses in personal care, cosmetic, detergent, as well as other household and industrial uses.

2. Description of Related Art

Process Background

The reaction of a reducing saccharide, e.g. an aldose or ketose saccharide, or a source thereof, with an alcohol result in the formation of a glycoside. Acids catalyze the reaction between a reducing saccharide and an alcohol. When the alcohol is an alkanol, the resulting glycoside is commonly referred to as an alkyl glycoside or an alkylpolyglycoside. These glycosides are useful for a wide range of applications depending on their hydrophilic-lipophilic balance (HLB). These properties are known to be influenced by the length of the alkyl chain and degree of polymerization (DP) of the glycoside product. Alkylpolyglycosides have been prepared by a variety of methods in laboratory, semi-commercial and large scale commercial process techniques. Primary commercial emphasis has focussed on the preparation of $C_8$–$C_{18}$ glucosides by the reaction of a suitable $C_8$–$C_{18}$ alcohol or available mixtures thereof with a saccharide reactant (e.g., a monosaccharide or a material hydrolyzable to a monosaccharide) at an elevated temperature in the presence of a suitable acid catalyst. U.S. Pat. No. 4,987,225 contains an extensive listing of processes for preparing alkyl glycoside compositions. As disclosed therein, processes for preparing alkyl glycoside compositions are disclosed in U.S. Pat. No. 3,219,656 to Boettner (issued Nov. 23, 1965); U.S. Pat. No. 3,547,828 to Mansfield et al. (issued Dec. 15, 1970); U.S. Pat. No. 3,598,865 to Lew (issued Aug. 10, 1971); U.S. Pat. No. 3,707,535 to Lew (issued Dec. 26, 1972); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sept. 14, 1982); U.S. Pat. No. 4,393,203 to Mao et al. (issued Jul. 12, 1983); U.S. Pat. No. 4,472,170 to Hellyer (issued Sept. 18, 1984); U.S. Pat. No. 4,510,306 to Langdon (issued Apr. 9, 1985); U.S. Pat. No. 4,597,770 to Forand et al. (issued Jul. 1, 1986); U.S. Pat. No. 4,704,453 to Lorenz et al. (issued Nov. 3, 1987); U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No. 0096917; Farris; published Dec. 28, 1983); and published European Application No. 84303874.6 (EPO Publication 0132043; published Jan. 23, 1985).

During the course of the aforementioned acid-catalyzed saccharide reactant/long chain alcohol reaction there is usually employed a substantial stoichiometric excess of the long chain alcohol reactant. The resulting reaction product mixture as initially made (i.e., without any intervening separation, fractionation or purification operations) typically contains a substantial quantity of residual unreacted long chain alcohol, the monoglycoside of the long chain alcohol as the predominant glycoside molecular species on a mole percentage basis, the various higher degree of polymerization long chain alcohol polyglycoside species in progressively decreasing mole percentage amounts or proportions principally from the DP2 through DP10 glycosides. Depending on factors including selection of the desired product and process economics, it is known to control process conditions such as temperature, select catalysts of varying hydrophobic character and refine the product by various techniques. For example, in accordance with the various prior art references, it is known to remove the residual unreacted long chain alcohol from the indicated reaction mixture via various techniques such as vacuum distillation, organic solvent (e.g. acetone) extraction or fractionation, and thin (or wiped) film evaporation. If the long chain (fatty) alcohol is removed from the reaction mixture by one of the distillation or evaporation methods, the polysaccharide by-products and any other materials with low volatility remain in the alkyl glycoside product.

In commercial practice, depending on process economics and the properties of the desired alkylpolyglycoside product, a variety of fatty alcohol reactants may be selected for the reaction. These alcohols include mono alcohols, i.e., those having primarily a single alkyl chain, binary alcohol mixtures, i.e., having primarily two different alkyl chains of different carbon chain lengths, and even ternary mixtures. Binary mixtures of alcohols are available commercially from natural sources as well as synthetic techniques and are employed commercially for the production of the corresponding mixtures of alkylpolyglycosides. Especially important binary alcohol mixtures include the $C_8$–$C_{10}$, $C_{10}$–$C_{12}$, $C_{12}$–$C_{14}$, and $C_{16}$–$C_{18}$ where the alkyl groups are derived from naturally occurring fats and oils. Important ternary mixtures include the $C_{12}$–$C_{14}$–$C_{16}$ or $C_{10}$–$C_{12}$–$C_{14}$ alcohols. The oxo alcohol technology is also employed which provides mixtures containing an odd number of carbon atoms in the alkyl chain, for example an oxo alcohol composed of a mixture of $C_9$, $C_{10}$ and $C_{11}$ alcohols or $C_{12}$ and $C_{13}$ as well. Other synthetic alcohols may be provided by Ziegler Chemistry in which ethylene is added to a triethylaluminum, which is then oxidized to an alkoxide, which is subsequently converted to a mixture of linear alcohols.

Applications or use Background

Since the practice of commercial scale processes for the production of alkylpolyglycoside products is governed chiefly by economic factors, it is not economically feasible to produce a wide variety of alkylpolyglycoside products for distribution in commerce. One important factor in the process economics is the need to employ and recycle excess alcohol in the reactor. This is unfortunate since the applications or end use of these compositions is highly dependent on combinations of factors including carbon chain length, degree of polymerization, and additional factors such as the co-presence of impurities or minor amounts of residual surfactants. A wide variety of applications of alkylpolyglycoside products is known in the prior art. Illustrations of such uses include hard surface cleaner compositions, U.S. Pat. Nos. 4,606,850, 4,627,931; polymerizations aids, U.S. Pat. No. 4,657,999; liquid soaps and bubble baths, U.S. Pat. No. 4,668,422; carpet shampoo and cleaning uses, U.S. Pat.

No. 4,678,595; corrosion inhibitors, U.S. Pat. No. 4,705,665; dishwashing detergents, U.S. Pat. No. 4,732,704; viscosity modifiers, U.S. Pat. No. 4,732,696; potentiating agents, U.S. Pat. No. 4,748,158; contact lens cleaning, U.S. Pat. No. 4,767,559; detergent and shampoos, U.S. Pat. Nos. 4,780,234, 4,565,647, 4,663,069, 4,483,779, 4,396,520, 4,599,188, 4,493,773, 4,536,319, 4,154,706, 4,304,679; and cosmetics, U.S. Pat Nos. 4,323,468, 4,196,201. This list is not intended to be all inclusive but merely to illustrate the wide variety of applications and end uses of alkylpolyglycoside compositions requiring specialized formulation considerations, which for the most part must be determined empirically.

Donald E. Koeltzow and Allen D. Urfer describe important physical and functional properties of relatively pure alkylpolyglycosides in "Preparation and Properties of Pure Alkyl Glucosides, Maltosides and Maltotriosides", JAOCS, Vol. 61, No. 10, pp. 1651–1655, October, 1984. Reference is also made to a publication by Francis A. Hughes and Book W. Lew, which describes physical and functional properties which render them suitable for use as biodegradable surfactants, emulsifiers and detergents, "Physical and Functional Properties of Some Higher Alkyl Polyglucosides", JAOCS, Vol. 47, pp. 162–167, 1970. Typically in the past, alkylpolyglycosides have required formulation with anionic or cationic surfactants to provide for enhanced detergent surfactant properties.

U.S. Pat. No. 4,668,422, noted earlier, dealing with liquid soaps and bubble baths, prepared formulations in examples 6, 7 and 11 in which mixtures of two different alkylpolyglycosides were mixed in substantially equal amounts by weight, a $C_{9-11}$ alkylpolyglycoside having a DP of 1.3 and a $C_{12-13}$ alkylpolyglycoside having a DP of 2.8. At this substantially equal weight mixture no improvement is shown for examples 6, 7, or 11 over examples 1, 2, or 12 employing only one of the alkylpolyglycosides.

Similarly, in German Application DE 4 005 959, directed to liquid, foaming, cleaning agents, more specifically dishwashing detergents, an approach is taken whereby the mean degree of glycosidation (glycoside units per fatty alcohol residue) is not too high. The degree of glycosidation is controlled or determined by mixing two different alkylglycosides of differing alkyl lengths and differing degrees of glycosidation, in which each alkylpolyglycoside has an alkyl group of only one chain length, i.e. all $C_{10}$ and all $C_{11}$, or two different alkylpolyglycosides of mixed alkyl groups, i.e. $C_{8-10}$ and $C_{11-18}$, in which 1–10 parts of the $C_{11-18}$ is mixed with 1 part of $C_{8-10}$. Specifically shown are mixtures of $C_8C_{10}G_{1.8}$ with a $C_{12}C_{14}G_{1.2}$ or $C_{12}C_{13}G_{1.1}$.

More recently, however, Japanese Patent Application No. 63-298821 filed 25 Nov. 1988 and laid open Jun. 5, 1990 (Kokai No. 145696/90) describes a higher alkylglycoside composition said to possess foaming characteristics equivalent to general purpose anionic surfactants, such as sodium dodecylbenzene sulfonate and sodium polyoxyethylene (3EO) dodecyl sulfate. The formulated compositions are described as a mixture of individual or pure higher alkylglycosides characterized in an essential component of at least 14% by weight of component (A) a decyl or/and (B) an undecyl polyglycoside with at least 14% by weight of component (C) a dodecyl or/and (D) a tridecyl polyglycoside in which (A) has an average degree of polymerization (DP) of 1.1 to about 4.1; (B) has an average DP of 1.4 to about 2.5; (C) has an average DP of 2.4 to about 3.8 and (D) has an average DP of 2.9 to about 4.6. Both the number of alkyl carbon atoms and the DP are described as (5) essential, particularly for component (A). Compositions are described comprising 28–92% by weight of (A) with the remainder being alkylglycosides having non-essential alkyl glycosides having alkyl groups of 11–14 and higher. Described are:

(1) mixtures of (A) with (i) n-hexadecylglycoside or (ii) n-tetradecylglycoside (as non-essential components);
(2) a mixture of (A) with a dodecylglycloside having a DP of 1.8, outside the DP range for component (C) above as a non-essential component; and
(3) mixtures of one or two of essential components (A) through (D) above with one non-essential component (either an alkyl group other than 10–13 carbon atoms or a DP outside the range for the essential components).

While the approach of the Japanese reference to mix glycosides of individual, single, alkyl groups could allow simulation of foaming surfactant properties, unfortunately, the use of mixtures of alkylpolyglycosides derived from readily available binary mixtures of fatty alcohols as described above are not encompassed within the teachings of the Japanese reference. The mixtures of alkylpolyglycosides derived from mono or relatively pure cut alcohols suggest a completely different approach than the unique, surprising and economically practicable approach hereinafter described with reference to the present invention.

In another approach, European Patent Application, EP 92355, published Oct. 26, 1983, describes the preparation of fatty glycoside mixtures by reaction of a saccharide-containing composition of the formula $A$—$O$—$(G)_x$, where A is hydrogen or an organo group of less than 8 carbon atoms, G is a saccharide and x is an integer of at least 1, with a lipophilic alcohol having at least 8 carbon atoms and a surfactant additive of the formula $R_fO(G)_n$, where $R_f$ is a lipophilic organo group having at least 8 carbon atoms, G is a saccharide unit and n is an integer of at least 1. The reaction may be controlled to promote fatty glycoside mixtures of varying degrees of glycosidation. The applicants indicate generally that the mixture may be fractionated into divergent fatty glycoside fractions of differing HLB values, which may be recombined to make a fatty glycoside mixture of predetermined HLB values. No specific example of such a mixture is given. This approach, using individual divergent fractions, is similar to the Japanese approach of combining glycosides of individual, single, alkyl groups.

Description of the Invention

Other than in the operating examples, or where otherwise indicated, all numbers expressing quantities of ingredients or reaction conditions used herein are to be understood as modified in all instances by the term "about".

It is an object of the present invention to overcome and eliminate the shortcomings and disadvantages inherent in prior methods and compositions of alkylpolyglycosides and to provide alkylpolyglycoside compositions having the combination of physical and functional properties desired for use in a wide range of end uses including cosmetic, personal care and cleaning applications. It is a further, more specific object to generally enable the preparation of alkylpolyglycoside compositions having preselected or predetermined average alkyl chain length from readily available primarily binary or ternary mixtures of alkylpolyglycosides. It is still a further object to prepare alkylpolyglycoside mixtures having an average alkyl chain length between $C_{10}$ and $C_{11}$ from reactants of natural origin for application in non-irritating cleaning and cosmetic applications.

It has now been discovered that an alkylpolyglycoside composition having a preselected or predetermined average alkyl chain length and surfactant properties can be prepared from the at least binary mixture alkylpolyglycoside compositions prepared commercially as described above. After selecting the predetermined average carbon chain length of the alkyl moiety, the composition having the desired detergent or surfactant properties is prepared by mixing two or more of at least binary components, each binary component having an average alkyl chain length such that when mixed the amounts of the binary components are effective to provide the predetermined selected average alkyl moiety and the surfactant properties.

By "at least binary component" as the term is employed herein is meant to include compositions having at least two different alkyl chain length polyglycosides, and accordingly includes ternary mixtures containing three different alkyl chain length polyglycosides. Thus, the composition may contain a mixture of $C_8$–$C_{10}$, $C_{10}$–$C_{12}$, $C_{12}$–$C_{13}$, $C_{12}$–$C_{16}$, $C_{12}$–$C_{14}$, $C_{14}$–$C_{15}$, $C_{16}$–$C_{18}$, as well as one containing $C_9$–$C_{10}$–$C_{11}$, $C_{12}$–$C_{14}$–$C_{16}$ alkylpolyglucosides, or the like.

Unexpectedly, it was found that mixing the at least binary compositions having differing alkyl moieties as described above affords an opportunity to formulate to a wide variety of desired and preselected surfactant or detergent properties and provides for improved overall properties of the mixture. It was also found that where the mixture is formulated by the approach of the present invention to provide improved or superior foaming properties, unexpectedly the mixture provides for improved critical micelle concentration (CMC) and interfacial tension (IFT) properties, which are useful properties for textile detergency, emulsification, solubilization and a variety of other properties for surfactant activity. The broad base of alkyl groups in the mixture of lower alkyl and higher alkyl further provide for improved solubility especially in caustic or other solutions containing builders or electrolytes.

Accordingly, the present invention affords a unique and surprising approach to preparing alkylpolyglycoside compositions having a designated average alkyl chain length, which chain length has a predominant impact on HLB and other properties. By taking any two or more binary components and mixing these to provide a designated average alkyl chain length, surprisingly and unexpectedly it was found that the composition retains the beneficial effects of each of the binary components while providing the desired HLB and surfactant properties. This approach is in contrast to the approach of the Japanese reference employing pure, single or individual alkylglycosides with the deficiencies attendant thereto. The present invention further affords the advantageous opportunity to utilize the commercial binary or ternary product mixtures prepared from the myriad of alcohols commercially available either derived from natural resources, fats and oils which are preferred from an environmental viewpoint being a renewable source of raw material; or derived "synthetically" through conversion of petrochemical sources such as in the Ziegler process or oxo process.

Figure 1:
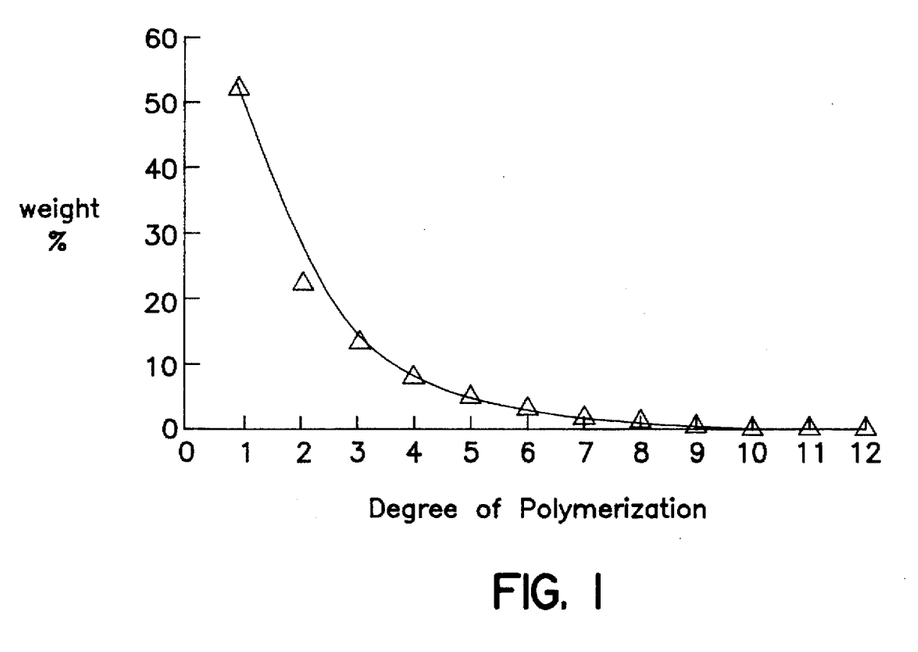

The starting products for preparing the mixtures of the alkylpolyglycoside compositions of the present invention are those described in the related art section above, in which the initial reaction product of the alcohol and saccharide in the presence of an acid catalyst results in a mixture of a monoglycoside of the alcohol and various higher degrees of polymerization (DP) polyglycosides in progressively decreasing amounts, i.e., the diglycoside (DP2), the triglycoside (DP3) and the higher polyglycosides (DP4 and higher). The typical distribution of the various fractions is a Flory distribution, such as seen in FIG. 1. While the various fractions specific distribution may vary somewhat for various reaction products, the overall distribution curve seen in FIG. 1 is the same, though the average DP of the reaction mixture may vary due to the differing distribution of the various fractions DP1, DP2, DP3 and higher fractions. Typically, the Flory distribution of the reaction product after removal of the excess alcohol will have an average degree of polymerization above 1.2, i.e., typically about 1.4, with a monoglucoside content in the range of about 50–70% by weight of the glycoside product, up to about 2.8, preferably up to about 2.0.

The glycoside products of the reaction of an alcohol and saccharide may be represented by the formula $$ROG_x$$

wherein R is a residue of an alcohol, O is oxygen, G is a glycoside residue, and x is the average degree of polymerization (DP) resulting from the various mono, di-, tri- and higher glycoside fractions present in the product and is a number of about 1 to about 3. The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycoside having corresponding more rings, the average of which in the product therefore being typically greater than about 1, generally in the order of about 1.2 to about 2.8, with preferred mixtures at about 1.4 to about 2.5.

The alkylpolyglycoside products represented by the formula above contain a lipophilic group, the R group, and a hydrophilic group, the $OG_x$ group. For detergent surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_o)}{(([MW_{AGU}] \times DP + MW_o) + MW_R)} \times 100/5$$

where AGU is typically the anhydro glucose unit in G having a molecular weight ($MW_{AGU}$) of 162 $MW_R$ is the molecular weight of the lipophilic group R, $MW_o$ is 16, the molecular weight of oxygen, and DP is the average degree of polymerization as predicted by Flory's statistical treatment. The present invention provides a method of preparing alkylpolyglycoside compositions having the most desirable HLB for detergent-surfactant use applications with the R group having a preselected average carbon chain length obtained by mixing at least two alkylpolyglycosides having R groups of lower carbon chains than the preselected R group and at least two alkylpolyglycosides having R groups of higher carbon chains than the preselected R group carbon chain.

The lipophilic R groups in the alkylpolyglycosides are accordingly derived from alcohols, preferably monohydric, which should contain from about 6 to about 20, preferably about 8 to about 18 carbon atoms, to provide R groups of sufficient length for detergent surfactant use applications. While the preferred R groups are saturated, aliphatic or alkyl groups, there may be present some unsaturated aliphatic hydrocarbon groups. Thus, the preferred groups are derived from the fatty alcohols derived from naturally occurring fat and oils, such as octyl, decyl, dodecyl, tetradecyl, hexadecyl, octadecyl, oleyl and linoleyl, but R groups may be derived from synthetically-produced Ziegler alcohols or oxo alcohols containing 9, 10, 11, 12, 13, 14, or 15 carbon atoms. The alcohols of naturally occurring fatty acids typically contain an even number of carbon atoms and mixtures of alcohols are commercially available such as mixtures of $C_8$ and $C_{10}$, $C_{12}$ and $C_{14}$, and the like. Synthetically-produced alcohols, for example those produced by an oxo process, contain both an even and an odd number of carbon atoms such as the $C_9$, $C_{10}$, $C_{11}$ mixtures of which are also available commercially.

Saccharide reactants which can be employed to prepare the aforementioned glycoside surfactants include reducing monosaccharide materials containing 5 or 6 carbon atoms such as for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, zylobiose, melibiose, cellobiose, raffinose, stachyose, etc.) and polysaccharides such as starch. Such saccharide reactants may be employed in dry (e.g. anhydrous) form or, if desired, may be employed in the hydrated form. If utilized in the hydrated form, it is preferred that the reaction mixture contain only small amounts of water, i.e., less than about 1% by weight, preferably less than about 0.5%, i.e. less than 0.25 or 0.1%.

While the preparation of the initial alkyl glycosides employed in the present invention form no part of the present invention, a brief description generally of the preparation follows. The molar ratio of alcohol to saccharide is typically between about 1.5:1 to about 10:1 to provide the production of an alkyl glycoside product having a DP between about 1.2 to about 2.8, preferably about 1.4 to about 2.5. The reaction is conducted at elevated temperatures from about 80° to about 140° C., preferably about 90° to about 120° C., and at pressures (about 10 to about 100 mm Hg absolute), which facilitate water removal, while at the same time maintaining the desired reaction temperatures. The reaction is conducted in the presence of an acid catalyst which may include strong mineral acids such as hydrochloric acid, sulfuric acid, nitric acid, phosphoric acid, hypophosphorous acid, etc., strong organic acids such as para toluenesulfonic acid, methanesulfonic acid, triflouromethanesulfonic acid, mono- or polyalkylated aryl mono- or polysulfonic acids such as dodecylbenzenesulfonic acid, etc. Upon completion of the reaction, the acid catalyst is neutralized by an alkaline material such as sodium hydroxide on essentially a stoichiometric basis. After neutralization, the excess unreacted alcohol is removed typically by evaporation or distillation, i.e., a wiped film evaporator, at about 160° to about 200° C. at about 0.1 to about 3 mm Hg pressure to levels below about 5%, more desirably below about 2% to about 0.5% by weight.

At this point, the resulting product commercially, substantially devoid of alcohol, is typically a binary mixture of alkyl glycosides, in which for purposes of this invention the alkyl group will contain from about 6 to about 20, preferably about 8 to about 18, carbon atoms, having the typical Flory distribution discussed earlier above.

As indicated earlier, the alkyl glycoside compositions of this invention are prepared by mixing two or more of at least binary components containing alkylpolyglycosides of varying alkyl chain lengths in amounts to provide surfactant properties of a preselected average alkyl chain length. This is preferably achieved by mixing at least two binary components, one of which has an average alkyl chain length below the preselected average alkyl chain length and the other binary component has an average alkyl chain length greater than the preselected average chain length. Thus, if an alkylpolyglycoside of the preselected average alkyl chain length desired, which may be designated as $R_{sp}$ herein, has a chain length of N number of carbon atoms, one binary component will have a lower average chain length alkylpolyglycoside, in which the R group may be designated as $R_c$, will have less than N number of carbon atoms (i.e., $R_c < R_{sp}$), while the other binary component will have average higher chain length alkyl groups, which may be designated $R_{hc}$, and will have more than N number of carbon atoms (i.e., $R_{hc} > R_{sp}$). In a preferred embodiment there is a difference of at least one carbon atom between the lower and higher average chain lengths of the binary components being mixed to attain surfactant properties of a product having the preselected chain length.

In carrying out one embodiment of the process of the present invention and prepare the alkylpolyglycoside of the present invention, it was found unexpectedly that the resulting product possessed the high solubility of the mixture of lower chain length polyglycosides and the surface properties, i.e. low critical micelle concentration of the mixture of the higher chain length polyglycosides but unexpectedly provided greater foam properties than either of the starting mixtures of lower or higher chain length polyglycosides.

Since the resulting compositions of the mixture is reached by mixing at least two binary components having a lower average chain length, with individual glycoside chain length of about 8 to about 18, and a higher average chain length, the resulting average chain length preselected will lie in the range of about 9 to about 14, preferably about 9 to about 12. For surfactant properties, the HLB of the resulting from the mixtures composition will have a range of about 10 to about 16, and preferably about 11 to about 14. The average DP of the composition resulting from the mixture will be in the range of about 1.2 to about 3, preferably in the range of about 1.4 to about 2.5.

The following examples serve to illustrate, but not limit, the invention. All parts and percentages are by weight, unless otherwise noted. In the examples to follow, commercially available alkylpolyglycosides available from Henkel Corporation were employed, as follows:

1. APG® Surfactant 225—an alkylpolyglycoside in which the alkyl group contains 8 and 10 carbons from a mixture of mixed $C_8$ and $C_{10}$ alkanols, in which the alkyl chain by weight % contains 45% $C_8$ and 55% $C_{10}$, and having an average DP of 1.6, an average lipophile chain (alkyl group), i.e., R equal to 9.1 and an HLB of 13.6.

2. APG® Surfactant 325—an alkylpolyglycoside in which the alkyl group are a mixture of $C_9$, $C_{10}$ and $C_{11}$ chains in a weight ratio respectively of 20:40:40, having an average DP of 1.6, an average lipophile chain of 10.2 and an HLB of 13.1.

3. APG® Surfactant 625—an alkylpolyglycoside in which the alkyl groups are a mixture of $C_{12}$, $C_{14}$ and $C_{16}$ chains in a weight ratio respectively of 68:26:6, and having an average DP of 1.6, an average lipophile chain of 12.76 and an HLB of 12.1.

4. APG® Surfactant 300—an alkylpolyglycoside substantially the same as the 325 product above but having an average DP of 1.4 and an HLB of 12.6.

5. APG® Surfactant 600—an alkylpolyglycoside substantially the same as the 625 product above but having an average DP of 1.4 and an HLB of 11.5.

EXAMPLE 1

In this example, a composition to be prepared from the commercially available APG® 225 and 625 surfactants above, was selected to substantially equal the alkyl average chain length of 10.2 of the 325 product produced from an oxo alcohol mixture containing alkyl groups containing both an even and an odd number of carbon atoms but employing alkylpolyglycosides from natural alkanols containing even number of carbon atom chains. The APG® 225 product containing a mixture of short chain $C_8$ and $C_{10}$ chain lengths was mixed with APG® 625 containing a mixture of long chain $C_{12}$, $C_{14}$ and $C_{16}$ chain lengths in a 2:1 ratio by weight to provide a resulting product having an average carbon chain length of 10.3, a calculated HLB of 13.1.

The product was evaluated by the following tests:

1. Ross Miles Foam—ASTM No. D1173-53. Foaming characteristics are measured of 0.1% active solutions made with deionized (DI) water in an apparatus that drops a 200 ml sample into 50 ml of the same solution. The test solutions are evaluated at 25° and 49° C. and the foam generated is measured in millimeters (mm) at 1 minute and again after an additional 5 minutes.

2. Blender Foam—measures the foaming properties with high agitation.
   a. Foam height is determined by measuring (in mm) the quantity of foam generated by 100 ml. of 0.9% active solutions mixed at high speed in a blender for 1 min. The test is run at 25° C. and uses water containing 150 ppm water electrolytes.
   b. Foam separation measures how quickly (in sec) 50% of the liquid phase (the 100 ml. test sample described above) is recovered from the foam phase.
   c. Foam flow measures the body of the foam by using 200 ml. of the same solution (0.9% actives) that is mixed in a blender for 1 min. The blender is opened and held inverted for 15 seconds over a funnel which is resting on a 20-mesh sieve. The funnel is modified with a wire across the diameter, 8 cm from the bottom. The time is recorded (in sec) from when the blender is inverted until the wire in the funnel becomes visible as the lather drains out.

3. Draves Wetting—ASTM No. D2281-68. The wetting ability of the surfactants is measured by the time it takes for a 0.1% active solution in DI water at pH 7 to completely saturate a cotton skein allowing it to sink in a 500 ml graduated cylinder.

4. CMC—The critical micelle concentration (CMC) was determined by the Wilhemy Plate Method using a Cahn Balance.

5. IFT—Interfacial tensions were measured using the spinning drop technique with mineral oil. A Spinning Drop Interfacial Tensiometer, Model 500 from the University of Texas, measures the interfacial tensions of 0.1% active solutions in DI water as dynes/cm.

6. HLB—The Hydrophilic-Lipophilic Balance was calculated for each blend using the procedure of dividing the weight percent of the hydrophilic by 5.

The following Table 1 is a summary of the results comparing the blends of the 225 and 625 mixtures with that of the 325 product and of the individual 225 and 625 products.

TABLE 1

| Ratio<br>APG ® Surfactant | 325 | 225 | 2:1<br>(225:625) | 625 |
|---|---|---|---|---|
| Average Carbon Chain | 10.2 | 9.1 | 10.3 | 12.8 |
| ROSS MILES Initial | 140 | 140 | 140 | 110 |
| (25° C., mm) 5 min | 140 | 135 | 135 | 110 |
| ROSS MILES Initial | 190 | 160 | 190 | 175 |
| (49° C., mm) 5 min | 190 | 160 | 190 | 175 |
| Draves Wetting (sec) | 15 | 240 | 35 | 28 |
| HLB (calc) | 13.1 | 13.6 | 13.1 | 12.1 |
| CMC (weight %) | 0.0178 | 0.0285 | 0.00521 | 0.00346 |
| IFT, 0.1% (dyn/cm) | 1.6 | 2.9 | 1.0 | 1.1 |
| Blender Foam,Initial | 95 | 100 | 95 | 35 |
| (25° C., mm) 5 min | 80 | 90 | 80 | 25 |
| Foam Separation (min) | 2:20 | 3:00 | 2:20 | 1:45 |
| Foam Flow (sec) | 3 | 19 | 4 | 0 |

The foregoing shows that the 2:1 mixture of the 225 and 625 products is superior in foam properties to either of the 225 or 625 product alone while matching the characteristics of the 325 product. The CMC and IFT are significantly lower than the values for the 225 product and lower than the 325 product and about the same level of the 625 product. Thus, the 2:1 mixture product of the present invention, provides superior surfactant surface properties with low CMC and IFT.

EXAMPLE 2

In the same manner as Example 1, blends of the 225 and 625 products were made at other ratios up to 9:1 and evaluated. Table 2 below is a summary of the test results in which the 2:1 test data of Example 1 is also included along with the other ratios of 225:625 as shown.

TABLE 2

| APG ® Surfactant Ratios | 325 | 225 | 225:625 | | | | | 625 |
| | | | 9:1 | 4:1 | 3:1 | 2:1 | 1:1 | |
|---|---|---|---|---|---|---|---|---|
| Average Carbon Chain | 10.2 | 9.1 | 9.5 | 9.8 | 10.0 | 10.3 | 11.0 | 12.8 |
| ROSS MILES Initial | 140 | 140 | 135 | 135 | 140 | 140 | 140 | 110 |
| (25° C., mm) 5 min | 140 | 135 | 130 | 130 | 135 | 135 | 140 | 110 |
| ROSS MILES Initial | 190 | 160 | 200 | 200 | 195 | 190 | 195 | 175 |
| (49° C., mm) 5 min | 190 | 160 | 190 | 195 | 190 | 190 | 190 | 175 |
| Draves Wetting (sec) | 15 | 240 | 75 | 38 | 36 | 35 | 32 | 28 |
| HLB (calc) | 13.1 | 13.6 | 13.4 | 13.3 | 13.2 | 13.1 | 12.8 | 12.1 |
| CMC (weight %) | 0.0178 | 0.0285 | — | — | — | 0.00521 | — | 0.00346 |
| IFT, 0.1% (dyn/cm) | 1.6 | 2.9 | — | — | — | 1.0 | — | 1.07 |
| Blender Foam, Initial | 95 | 100 | 105 | 105 | 100 | 95 | 85 | 35 |
| (25° C., mm) 5 min | 80 | 90 | 90 | 90 | 90 | 80 | 80 | 25 |
| Foam Separation (min) | 2:20 | 3:00 | 2:50 | 2:35 | 2:35 | 2:20 | 2:00 | 1:45 |
| Foam Flow (sec) | 3 | 19 | 11 | 7 | 4 | 4 | 3 | 0 |

EXAMPLE 3

In this example the 2:1 mixture of the 225 and 625 products were evaluated for caustic solubility at 25° C. The results are shown in Table 3, in which data for the 225, 325 and 625 products individually are also shown. The percentage of each alkylglycoside that is soluble in the various levels of caustic (NaOH) is shown. Solubility is qualified as the level of glycoside which results in a clear, homogenous solution.

TABLE 3

| APG ® | % APG in | | | | |
|---|---|---|---|---|---|
| | 0% NaOH | 10% NaOH | 20% NaOH | 30% NaOH | 40% NaOH |
| APG ® 225 | 73 | 60 | 45 | 35 | 28 |
| APG ® 325 | 56.5 | 41.5 | 24.5 | 14 | 5.5 |
| 225/625 (2:1) | 64.5 | 53 | 43 | 34 | 26 |
| APG ® 625 | 33 | 25 | 11 | 2 | 0 |

The foregoing illustrates the superior solubility of the mixture of at least two lower short chain with at least two higher or longer chain glycosides which provides a broader base of fatty chains from $C_8$ to $C_{16}$ in the product in contrast to the individual narrower base of the individual 225, 325 or 625 polyglycoside products. This advantage in solubility indicates the suitability of the 225:625 mixture in the 2:1 ratio by weight in hard surface cleaning formulations such as the following:

| Ingredient | Wt % |
|---|---|
| HEAVY DUTY - ALL PURPOSE CLEANER | |
| Water | 80 |
| Tetrapotassium Pyrophosphate | 5 |
| Sodium Metasilicate Pentahydrate | 3 |
| Sodium Hydroxide (50%) | 2 |
| Sodium Xylene Sulfonate (40%) | 5 |
| Alkylpolyglycoside (50%) | 5 |
| ALUMINUM CLEANER - ALKALI | |
| Water | 58 |
| Sodium EDTA | 2 |
| Sodium Gluconate | 2 |
| Sodium Silicate ($SiO_2/Na_2O$ = 2.5) | 20 |
| Potassium Hydroxide (45%) | 15 |
| Alkylpolyglycoside (50%) | 3 |

In the foregoing cleaning formulations, the alkylpolyglycoside of the present invention is employed with adjuvants commonly or usually associated with cleaner applications. The alkylpolyglycoside is employed alone, or preferably, with other co-surfactants, particularly anionic surfactants, such as ethoxylated, or unethoxylated, long chain (8 to 22 carbon) alcohol sulfates or sulfonates.

EXAMPLE 4

A Gardner cleaning evaluation ASTM No. D4488-85 was conducted for 3:1, 2:1 and 1:1 blends of the 225 and 625 product, in which mechanical soil removal tests were performed to measure the relative ability of the surfactants to remove a standard soil (A3) from white vinyl tiles using a Gardner Straight Line Washability Machine. The procedure utilizes a Labscan Reflectometer to measure the initial reflectance of clean white vinyl tiles prior to soiling and then after washing with a sponge for 20 cycles in test solutions of 0.6% active surfactant in DI water at 25°C.

The calculation is typical for this type of cleaning test where the cleaning ability of water alone is used as the baseline:

$$\% \text{ SOIL REMOVED} = \frac{RF - RH_2O}{RI - RH_2O} \times 100$$

RF=Reflectance of the washed tile
RI=Initial reflectance of the unsoiled tile
$RH_2O$=Reflectance of the tile washed in water only The results of the test showed the blends to be slightly less effective than the 325 alone, but the 3:1 and 2:1 blends are within the 3% of soil removal requirement.

The foregoing examples illustrate the method of preparing compositions of the present invention. Specifically, a selection of a predetermined average alkyl chain length of about 10.2 (above about 9 and below about 12) was made for the alkyl moiety to provide a surfactant composition having an HLB of about 13 and a DP of about 1.6. The predetermined or selected composition was then prepared by mixing or blending a mixture of a $C_8$ and $C_{10}$ alkylpolyglycoside (alkyl group lower in chain length than the selected average chain length of 10.2) with a mixture of a $C_{12}$, $C_{14}$ and $C_{16}$ alkylpolyglycoside (alkyl group higher in chain length than the selected chain length of 10.2). The resulting products in ratios of up to 9:1 of the lower and higher chain length provided a surfactant composition having an HLB of about 13 and exhibiting foam properties superior to the individual mixtures of $C_8$ and $C_{10}$ alone or the $C_{12}$, $C_{14}$ and $C_{16}$ alone, with low CMC and IFT properties. The products have superior solubility in caustic thus providing compositions which can be formulated into hard surface cleaner compositions. The products can also be formulated for soil removal or laundry detergent compositions. The compositions also find utility in widely diverse applications such as coal dust suppressant compositions, flotation of ores, particularly non-sulfidic ores such as cassiterite, corrosion inhibitor compositions and contact lens cleaning compositions.

The compositions also have surfactant properties particularly suitable for use in the cosmetic industry for formulation into personal care products, including mild shampoos and mild children's liquid soaps, as well as lotions, creams. The compositions are particularly useful in toothpastes and mouthwash formulations as well as antiperspirant applications.

EXAMPLE 5

In this example, blends of two binary fractions were evaluated to provide an alkylpolyglycoside composition having surfactant properties suitable for cosmetic industry application. The test method employed in the evaluation was a foam method acceptable to the cosmetic industry, which is carried out with, and without the use of a synthetic sebum composition. The foam test methodology is as follows:

Prepare a 10% aqueous solution of product being evaluated. Add four (4) grams of this solution to 146 grams of water (hardness 50 ppm) heated to 29° C. ±1° C. Agitate for five (5) seconds in a Sears electronic blender with microprocessor control, medium/No. 5 speed agitation. Transfer the foam into a 500 ml graduated cylinder. Measure the initial foam volume to the nearest 5 ml and then record the position of the foam/water interface after 3.5 minutes. This later reading represents the foam drainage.

When testing with synthetic sebum, 0.5 grams synthetic sebum is added to product prior to preparing the 10% aqueous solution, after which the test is run as described above. The synthetic sebum employed has the following composition.

| Ingredient | % by Weight |
|---|---|
| Palmitic Acid | 10.00 |
| Stearic Acid | 5.00 |
| Coconut Oil | 15.00 |
| Paraffin | 10.00 |
| Spermaceti | 15.00 |
| Olive Oil | 20.00 |
| Squalene | 5.00 |
| Cholesterol | 5.00 |
| Oleic Acid | 10.00 |
| Linoleic Acid | 5.00 |
|  | 100.00 |

In testing for foam the foam tests were repeated five times and an average taken. In the data in Table 5 below, the first figure reported is the foam height and the second reading is taken 3.5 minutes later and represents foam drainage.

TABLE 5

| Sample | | Foam Results | |
|---|---|---|---|
| Weight Ratio | Alkylpolyglycoside | With Sebum | Without Sebum |
| 4:1 | APG 225/625 | 250/140 | 255/140 |
| 3:1 | " | 265/135 | 260/145 |
| 2.5:1 | " | 265/135 | 265/145 |
| 2:1 | " | 267/135 | 275/135 |
| 1.5:1 | " | 270/135 | 275/135 |
| — | APG 225 | 190/142 | 200/140 |
| — | APG 300 | 280/135 | 290/137 |
| — | APG 325 | 260/135 | 275/135 |
| — | APG 625 | 240/145 | 260/145 |
| — | APG 600 | 250/145 | 255/140 |
| 4:1 | APG 225/APG 600 | 265/135 | 270/135 |
| 3:1 | " | 275/135 | 270/135 |
| 2.5:1 | " | 277/135 | 285/135 |
| 2:1 | " | 280/135 | 290/137 |
| 1.5:1 | " | 280/135 | 290/135 |

From the foregoing, it can be seen that employing weight ratios of 2:1 or 1.5:1 of the 225 binary fraction with the APG® 600 or 625 ternary fractions a composition results which meets the foaming properties of the APG® 300 or 325 products which find utility in the cosmetic industry. The data also indicates a degree of synergism in weight ratios up to about 4:1, providing a means for formulating compositions using commercial products comprised of at least binary mixture or fractions, to designated desired average carbon chain lengths and desired HLB values. With the range of about 1.5:1 to about 4:1 of the APG® 225 (which contains 45% $C_8$ and 55% $C_{10}$) to the APG® 625 (which contains 68% $C_{12}$, 26% $C_{14}$ and 6% $C_{16}$), the $C_{10}$ species will predominate in the mixture, which species will predominate in any mixture of APG® 225 and APG® 625, in which the weight ratio in the mixture of APG® 22.5 to APG® 625 is above about 1.25:1.

The examples above illustrate that significant results are achieved by the alkylpolyglycosides mixtures of the present invention, even in the absence of any co-surfactants. While the mixtures may be employed without added surfactants, their use in formulations for various end-use applications, provides for significant, advantageous properties in such formulations employing other co-surfactants. For example, anionic surfactants are generally highly irritative to the skin. However, when the alkylpolyglycoside mixtures of the present invention are employed in formulations employing anionic surfactants, it was found that the formulated composition was no longer highly irritative to the skin and, accordingly, the alkylpolyglycoside mixture of the present invention finds special utility in cosmetic, particularly personal care, products and applications, where mild or non-irritative properties are particularly desirable, such as shampoos, foam baths, hand soaps, hair conditioners, and facial cleansers. Thus the alkylpolyglycoside surfactant compositions of the present invention offer formulation ease with good foaming and cleaning power of an anionic surfactant and further offering mildness to skin and eyes. While noting their use with anionic surfactants, the alkylpolyglycoside surfactants of the present invention may stand alone on the primary surfactant or are also compatible with other surfactant types (including non-ionic, cationic and amphoteric), providing improved performance of the formulations therewith.

In end-use formulations, the alkylpolyglycosides resulting from the present invention, the polyglycoside will typically be present in amount from ½ to about 80% and more typically about 30, 50 or 70% in an aqueous solution form. A granule form of the alkylpolyglycoside may be prepared by spray drying an aqueous solution of the polyglycoside and adjuvants to provide a substantially dry, non-sticky granule. In such a product, the alkylpolyglycoside may comprise up to about 98–99% of the granule with very little water or other solvent, along with any optional adjuvants. The composition will utilize other compatible ingredients, which will vary dependent on the specific end-use application desired, the various end-use application having been discussed earlier referring to many patents. Thus, the compositions may contain in addition to other surfactants as co-surfactants, detergency builders, soil-suspending agents, brightening agents, abrasives, dyes, fabric-conditioning agents, hair conditioning agents, hydrotropes, solvents, fillers, etc. Such materials, usually associated with the specific end-use application desired, assist the alkylpolyglycoside in its end-use application, and are, accordingly, auxiliary, optional, reagents referred to herein as "adjuvants." Formulations for various end-use applications, accordingly, may generally comprise:

(a) alkylpolyglycoside surfactant of the present invention in an amount of about 0.5 to 99% by weight, (b) solvent (water or other non-aqueous liquid or mixtures thereof), in an amount of about 0.5 to about 99.5% by weight, and (c) adjuvant (optional ingredient based on particular end-use application) in an amount up to about 99.5% by weight.

The anionic surfactants include any of the surfactants commonly classified as anionic surfactants. These surfactants include the alkali metal, ammonium and magnesium salts of the alpha olefin sulfonates, alkyl sulfonates, alkyl aryl sulfonates, alkyl aryl ether sulfates, alkyl ether sulfates, sulfated alcohol ethoxylates, taurates, petroleum sulfonates, alkyl napthalene sulfonates, alkyl sarcosinates and the alkyl sulfosuccinates in which the alkyl group is preferably a long chain 8 to 22 carbon atom group and the aryl group is preferably phenyl or naphthyl. Typical surfactants which fall within the above description include sodium lauryl sulfonate, ammonium lauryl sulfonate, ammonium lauryl sulfate, dodecyl benzene sulfonate, sodium lauryl sulfate, sodium lauryl ether sulfate, sodium lauryl myristyl sulfate, diethanolamine lauryl sulfate, ammonium salts of sulfated alcohol ethoxylates, sodium cocoyl isethionate, sodium N-methyl-N-oleoyl taurate, sodium N-methyl-N-cocoyl taurate, triethanolamine lauryl sulfate, disodium monooleamide PEG-2 sulfosuccinate, petroleum sulfonates sodium salt, alkyl napthalene sodium sulfonates, sodium lauroyl sarcosinate, and sodium alkyl sulfosuccinate.

The amphoteric surfactants include the betaines, the sultaines, the imidazoline derivatives and the like. Typical amphoteric surfactants include ricinoleamidopropyl betaine, cocamidopropyl betaine, oleyl betaine, stearyl betaine, stearyl amphocarboxy glycinate, sodium lauraminopropionate, cocoamidopropyl hydroxy sultaine, disodium lauryliminodipropionate, tallowiminodipropionate, cocoampho- carboxy glycinate, cocoimidazoline carboxylate, lauric imidazoline monocarboxylate, lauric imidazoline dicarboxylate, lauric myristic betaine, cocoamidosulfobetaine, alkylamidophospho betaine and the like.

The nonionic surfactants preferably are the ethoxylated alcohols, including ethoxylated phenols. The preferred ethoxylated alcohols may be generally defined by the formula $R(OC_2H_4)_nOH$ where R is an alkyl chain of about 10 to about 18 carbon atoms and n is an average of from about 2 to about 9. Preferred alcohols are coconut alcohol, tallow alcohol and alcohols containing 12–16 carbon atoms, ethoxylated with about 6 to about 9 moles of ethylene oxide. Preferred phenols ethoxylated are the alkyl phenols containing about 6 to about 12 carbon atoms, preferably 8 to about 12 carbon atoms ethoxylated with about 5 to about 25 moles of ethylene oxide per mole of phenol, preferably about 9 to about 15 moles of ethylene oxide per mole of phenol.

The cationic surfactants which may be employed are quaternary ammonium types having at least one, and preferably two, long chain groups of about 8 to about 22 carbon atoms, preferably about 16 to 18 carbon atoms. The remaining groups are either hydrogen or preferably short chain alkyl or hydroxyalkyl groups in which the alkyl groups contain from about 1 to about 4 carbon atoms. Preferred cationic surfactants include di-tallowdimethyl ammonium chloride or methyl sulfate, and dicocodimethylammonium chloride.

In the examples to follow, the alkylpolyglycoside surfactant composition was a mixture of:

(a) 55.8 weight % of APG® Surfactant 200—an alkylpolyglycoside substantially the same as APG® 225 noted above in which the alkyl chain by weight contains 45% $C_8$ and 55% $C_{10}$ but having an average DP of 1.4; and (b) APG® Surfactant 600 earlier described, and containing 11.2% water. The mixture of the APG® 200 and APG® 600 alkylpolyglycosides (a weight ratio of the 200 to 600 alkylpolyglycoside of about 1.7) results in a mixture in which the $C_{10}$ species predominates. The product will be referred to in the subsequent examples as "Polyglycoside" employed as a 50% active solution in water.

In the conventional eye irritation test, when tested at 12% active solution, at pH 7.0, the 24-hour score is 8.0 on a scale of 0–110. Typically used anionic surfactants exhibit scores of about 30–35 in this test. In the conventional skin irritation test, at 12% active, pH of 7, the primary skin irritation index is 1.1 on a scale of 0–8. Typical anionic surfactants exhibit scores of about 4–6. Oral toxicity at 50% active, pH of 7, had 0% mortality at 5 grams per kilogram body weight, which is the cut-off point in the test.

EXAMPLE 6

This example illustrates a high-quality, high-performance shampoo that combines very low irritation with excellent foam characteristics, while leaving the hair in a very manageable condition. The ingredients and preparation are as follows:

TABLE 6

| Ingredients | % wt/wt |
| --- | --- |
| Polyglycoside | 15.0 |
| Ammonium Laureth Sulfate (Standapol ® EA-2)* | 15.0 |
| Cocamidopropyl Betaine (Velvetex ® BK-35)* | 12.5 |
| Hydrolyzed Collagen (Nutrilan ™ I)* | 1.5 |
| Citric Acid | to pH 6.0–6.5 |
| Fragrance | q.s.** |
| Water, preservative | Balance |

*available from Henkel Corporation
**quantity sufficient

The shampoo was prepared by charging the kettle with the water and adding the ingredients in the order listed while stirring. If necessary, the viscosity may be adjusted to the desired level by addition of sodium chloride. Gel-like viscosities can be obtained by adding a thickener, such as PEG-150 distearate.

EXAMPLE 7

This example illustrates a foam bath formulation which is combined with an ether sulfate to provide a foam bath with low irritation. The ingredients and preparation can be seen below:

TABLE 7

| Ingredients | % wt/wt |
| --- | --- |
| Sodium Laureth Sulfate (Standapol ® ES-3)* | 21.00 |
| Polyglycoside | 12.00 |
| Cocamidopropyl Betaine (Velvetex ® BA-35)* | 12.00 |
| Cocamide DEA (Standamid ® KD)* | 4.00 |
| Glycol Stearate (Emerest ® 2350)* | 2.00 |
| PEG-7 Glyceryl Cocoate (Cetiol ® HE)* | 1.00 |
| Cocoyl Sarcosine (Hamposyl C)** | 1.00 |
| Kathon CG*** | 0.05 |
| Fragrance & Dyes | q.s. |
| Water | Balance |

*available from Henkel Corporation
**available from Grace Co.
***preservative available from Rohm & Haas The foam bath was prepared by charging the kettle with the water and heating the water to 60°–65° C. While maintaining the temperature, the remaining ingredients are added one at a time with agitation. The pH is adjusted to 6.0–6.5, heating discontinued and the product permitted to cool to ambient temperature with continued stirring.

EXAMPLE 8

This example illustrates a mild facial cleanser combining a sulfosuccinate surfactant with the Polyglycoside. The oleyl betaine in the product functions as a skin conditioner. The ingredients and preparation can be seen from the following:

TABLE 8

| Ingredients | % wt/wt |
| --- | --- |
| Disodium Laureth Sulfosuccinate (Standapol® SH-124-3)* | 30.0 |
| Polyglycoside | 18.00 |
| Oleyl Betaine (Velvetex® OLB-50)* | 3.00 |
| PEG-120 Methyl Glucose Dioleate (Glucamate DOE-120)** | 2.25 |
| PEG-7 Glyceryl Cocoate (Cetiol® HE)* | 1.50 |
| Kathon CG*** | 0.05 |
| Fragrance & Dyes | q.s. |
| Water | Balance |

*available from Henkel Corporation
**available from Americhol
***preservative available from Rohm & Haas The facial cleanser was prepared by charging the kettle with water, heating the water to 40° C. and maintaining this temperature while adding the remaining ingredients one at a time with agitation. Heating is discontinued and stirring continued until the product reaches ambient temperature, after which the pH is adjusted to 6.0–6.5.

EXAMPLE 9

This example illustrates a liquid soap for application to human skin having high foaming and yet is mild to the skin. Two skin conditioners are included. The ingredients and preparation can be seen from the following:

TABLE 9

| Ingredients | % wt/wt |
| --- | --- |
| Sodium Lauryl Sulfate (Standapol® WAQ Special)* | 16.00 |
| Polyglycoside | 10.00 |
| Cocamidopropyl Betaine (Velvetex® BK-35)* | 3.50 |
| PEG-150 Distearate | 2.00 |
| PPG-12-PEG-65 Lanolin Oil (Lantrol® AWS 1692)* | 0.30 |
| Glycol Distearate (Emerest® 2355)* | 1.00 |
| Polyacrylamidomethylpropane Sulfonic Acid (Cosmedia® Polymer HSP-1180)* | 1.00 |
| Kathon CG** | 0.05 |
| Fragrance & Dyes | q.s. |
| Water | Balance |

*available from Henkel Corporation
**preservative available from Rohm & Haas

The liquid soap was prepared by charging the kettle with water, heating to 60°–65°C. and maintaining the temperature constant while adding the ingredients one at a time under agitation. Once uniform the heating is discontinued and stirring continued until the product reaches ambient temperature, after which the pH is adjusted to 6.0–6.5 with citric acid.

In this formulation, the Lantrol® AWS 1692 and the Cosmedia® Polymer HSP-1180 functions as skin conditioners.

In personal care products for application to human skin, such as a liquid soap above, it has recently become important to include in such soaps materials generally referred to as antimicrobial agents. The term "antimicrobial" as used herein is intended to encompass generally antibacterial, antiviral, antigermicidal agents and the like. It is important that such materials when employed in personal care products for use by humans be approved by the FDA (Food and Drug Administration). A commercially available antimicrobial agent is 5-chloro-2-(2,4-dichlorophenoxy) phenol, "Triclosan", manufactured by Ciba Geigy. Such antimicrobial agents when employed are added to the liquid soap in an amount of from about 0.25 to about 1% by weight, more desirably about 0.3 to about 0.5%. A wide variety of antimicrobial agents have been described and are available for various end-use applications. "Cation DDC", a recent antibacterial agent very effective against bacteria with high resistance, finds use in disinfection in restaurants and food processing centers. "Lebon 15" is a high molecular weight amphoteric surfactant that exhibits germicidal properties. Statutory Invention Registration H269 describes germicidal quaternary ammonium halides useful in disinfectant or sanitizing cleaner compositions. German published Application DE 3,316,250 A describes N-alkylated 1-amino-1-desoxy-D-fructo-pyranose antimicrobial agents effective against fungi and bacteria.

U.S. Pat. No. 4,900,721 describes disinfectants for skin and mucous membranes, which may contain one or more antimicrobial agents, such as quaternary ammonium compounds, phenols, biguanides and various others. U.S. Pat. No. 3,886,277 describes the use of 5,7-dichloro-8-hydroxy quinolines for controlling dandruff and in the background discussion describes a wide variety of substances exhibiting bacteriostatic and fungistatic properties including phenols, hexachlorophene, quaternary ammonium halides, and various sulfur-containing compounds (thio-bis compounds).

EXAMPLE 10

This example illustrates a low irritation conditioning shampoo in which the Polyglycoside enhances a cationic polymer deposition, providing a two-in-one conditioning shampoo. The ingredients and preparation can be seen from the following:

TABLE 10

| Ingredients | % wt/wt |
| --- | --- |
| Polyglycoside | 12.0 |
| Sodium Laureth Sulfate (Standapol® ES-2)* | 24.0 |
| Cocamide DEA (Standamid® KD)* | 3.0 |
| PEG-7 Glyceryl Cocoate (Cetiol® HE)* | 1.5 |
| Guar Hydroxypropyltrimonium Chloride (Cosmedia® Guar C-261)* | 0.75 |
| Glycol Distearate in a surfactant base (Euperlan® PK-810)* | 4.0 |
| Citric Acid | to pH 6.5 |
| Fragrance | q.s. |
| Water, preservative | Balance |

*available from Henkel Corporation

The conditioning shampoo was prepared by charging a kettle with the water and while stirring, adding the first three ingredients in the order listed. The next two ingredients are pre-slurried and then added to the kettle after which the Euperlan® ingredient is added. The pH is then adjusted with the citric acid and, if necessary, the viscosity is adjusted with sodium chloride or other viscosifiers.

The alkylpolyglycoside surfactant of the present invention may also be combined with an acyl isethionate surfactant, thereby providing good foaming or lathering and mildness to end uses where isethionate surfactants find utility. The isethionates find particular utility in soap bars. A typical soap bar will contain (a) from about 10 to about 80% by weight of the composition of a soap, of a synthetic, or natural fatty, acid containing from about 8 to about 18 carbon atoms;

(b) from about 10 to about 80% by weight of the composition of a $C_8$–$C_{18}$ fatty acyl isethionate as a non-soap surfactant;

(c) water; and optionally (d) adjuvants, such as pigments, perfumes, electrolytes and the like.

The alkylpolyglycoside surfactants of the present invention, i.e. the Polyglycoside, will be employed in combination with the isethionate and will result in less isethionate being necessary, but retaining, if not improving, lathering efficacy and providing mildness and non-irritation properties. The isethionate and alkylpolyglycoside are then co-surfactants and will be employed in the surfactant component in a weight ratio of alkylpolyglycoside to isethionate of about 10:1 to about 1:10, preferably about 5:1 to about 1:5.

As earlier indicated, the alkylpolyglycoside surfactant compositions of the present invention are useful in toothpaste, mouthwash and antiperspirant compositions. A typical toothpaste composition will contain from about 0.025 to about 2.5% by weight of alkylpolyglycoside. Toothpaste composition may typically also include polishing agents, antimicrobial agents, humectants, consistency regulators, flavoring oils and solubilizers, sweeteners and other optional adjuvants.

Where employed, the polishing agents are typically aluminum silicates, phosphates such as dicalcium phosphate, and ∝-aluminum oxide trihydrate, Al(OH)3, or weakly, calcined alumina containing about 20% by weight gamma-aluminum oxide and 80% by weight alpha-aluminum oxide. These are commercially available in various degrees of calcination, fineness and apparent density. Typical humectants include glycerol and sorbitol, which are preferred, propylene glycol and polyethylene glycols. Typical water-soluble consistency regulators include the nonionic polysaccharide derivatives such as methyl, hydroxypropyl, hydroxypropylmethyl and hydroxyethyl ethers of cellulose, starch, guar and vegetable gums. Where employed, the antimicrobial agents are typically antimicrobial biguanide compounds such as 1,1'-hexamethylene bis [5-(4-chlorophenyl)-biguanide], known as "chlorhexidine" and 1,1'-hexamethylene bis [5-(4-fluorophenyl)-biguanide], known as "fluorhexidine," employed in the form of a water-soluble, physiologically compatible salt, such as the acetate or glucanate.

EXAMPLE 11

The following are illustrative examples of toothpaste formulations employing the Polyglycoside product of the present invention as earlier described.

| Ingredient | % wt/wt |
|---|---|
| A. | |
| Polyglycoside | 4.0 |
| Magnesium Aluminum Silicate | 1.1 |
| Sodium Carboxymethylcellulose | 0.6 |
| Sorbitol (70% solution) | 10.0 |
| Glycerine | 15.0 |
| Dicalcium Phosphate.2H$_2$O | 46.0 |
| Flavor | 1.0 |
| Preservative | q.s. |
| Water | Balance |
| B. | |
| Polyglycoside | 4.0 |
| Hydroxypropyl Methylcellulose | 1.0 |
| Glycerine | 15.0 |
| Sorbitol (70% solution) | 15.0 |
| Calcium Carbonate | 10.0 |
| Dicalcium Phosphate.2H$_2$O | 40.0 |
| Flavor | 1.0 |
| Preservative | q.s. |
| Water | Balance |

A mouthwash composition will typically contain from about 0.005 to about 1% of alkylpolyglycoside in an aqueous, homogenous composition which may also contain up to about 20% by weight of ethanol. A typical mouthwash composition may also contain antimicrobial agents, flavoring oils and solubilizers, sweeteners and other adjuvants.

EXAMPLE 12

The following is an illustrative example of a mouthwash composition employing the Polyglycoside product of the present invention as earlier described.

| Ingredient | % wt/wt |
|---|---|
| Polyglycoside | 2.0 |
| Water | 80.762 |
| Ethanol | 17.0 |
| Sodium Saccharin | 0.15 |
| Spearmint Oil | 0.04 |
| Menthol | 0.04 |
| Cinnamon Oil | 0.008 |
| Dye | q.s. |

What is claimed is:

1. The method of preparing an alkylpolyglycoside surfactant composition having improved foaming properties along with low critical micelle concentration and low interfacial tension properties, in which the alkyl groups contain from about 6 to about 20 carbon atoms and in which the average alkyl chain length of the composition is from about 9 to about 14 and having a hydrophilic lipophilic balance (HLB) in the range of about 10 to about 16, comprising selecting a predetermined average carbon chain length of the alkyl moiety in the range of about 9 to about 14, for the composition and mixing two or more of at least binary components of alkylpolyglycoside, each binary component having an average alkyl chain length such that when mixed, the amounts of the binary components are effective to provide said predetermined selected average alkyl moiety and said improved foaming, critical micelle concentration and interfacial tension properties and wherein at least one, or all of the binary components comprises a Flory distribution of polyglycosides derived from an acid-catalyzed reaction of an alcohol containing 6–20 carbon atoms and a suitable saccharide from which excess alcohol has been separated, and wherein one of the binary components has an average alkyl chain length less than the predetermined selected average alkyl moiety for the composition and another binary component having an average alkyl chain length higher than said predetermined selected average alkyl moiety for the surfactant composition and in which the ratio by weight of the binary component having the average alkyl chain less than the predetermined selected average alkyl moiety to the binary components having an average alkyl chain higher than the predetermined selected average alkyl moiety is from 1.25:1 to about 10:1.

2. The method as defined in claim 1, wherein the average chain length of the alkyl chain in the product resulting from the mixture of the binary components is in the range of about 9 to about 12.

3. The method as defined in claim 1, in which said alkylpolyglycoside surfactant composition has an HLB of about 11 to about 14.

4. The method as defined in claim 1 in which the predetermined average alkyl moiety chain length is above 9 and the binary component having an average alkyl chain length less than the predetermined selected average alkyl moiety is present in the mixture in an amount in relation to another binary component having an average alkyl chain length higher than the predetermined selected alkyl moiety is effective to provide an average alkyl moiety chain length above 9.

5. The method as defined in claim 4, wherein said predetermined average alkyl moiety chain length is about 10.

6. The method as defined in claim 4, in which said binary component of alkylpolyglycoside having an average alkyl chain length less than the predetermined selected average alkyl moiety is a mixture of a $C_8$ alkylpolyglycoside and a $C_{10}$ alkylpolyglycoside.

7. The method as defined in claim 4 in which said binary component of alkylpolyglycosides having an average alkyl chain length higher than the predetermined selected alkyl moiety is a mixture of a $C_{12}$ alkylpolyglycoside, a $C_{14}$ alkylpolyglycoside and a $C_{16}$ alkylpolyglycoside.

8. The method as defined in claims 7 in which said binary component of alkylpolyglycosides having an average alkyl chain length less than the predetermined selected alkyl moiety is a mixture of a $C_8$ alkylpolyglycoside and a $C_{10}$ alkylpolyglycoside.

9. The method as defined in claim 8 in which the ratio by weight of the binary component of the $C_8$ and $C_{10}$ alkylpolyglycosides mixture to the binary component of the $C_{12}$, $C_{14}$ and $C_{16}$ alkylpolyglycosides mixture is about 1.25:1 to about 9:1.

10. The method as defined in claim 9 in which said ratio is above about 1.25:1 to about 4:1.

11. The method as defined in claim 9 in which said ratio is from about 1.5:1 to about 4:1.

12. The method as defined in claim 9 in which said ratio is about 1.7:1.

13. The method as defined in claim 9 in which the average alkyl chain length of the surfactant composition is about 10.3 and the HLB of the composition is about 13.

14. The method as defined in claim 9, in which the binary component of the $C_8$ and $C_{10}$ alkylpolyglycosides mixture comprises by weight about 45% $C_8$ and about 55% $C_{10}$; the $C_{12}$, $C_{14}$ and $C_{16}$ component comprises by weight about 68% $C_{12}$, about 26% $C_{14}$ and about 6% $C_{16}$, and the components are mixed in a weight ratio of about 58 parts $C_8C_{10}$ component to 33 parts $C_{12}C_{14}C_{16}$ component thereby providing an alkylpolyglycoside composition in which the $C_{10}$ species predominates.

15. The method of claim 1 wherein both binary components having the Flory distribution of polyglycosides contain less than about 5% by weight residual alcohol from said acid-catalyzed reaction.

16. An alkyl polyglycoside surfactant composition having improved foaming properties along with low critical micelle concentration and low interfacial tension properties, in which the alkyl moiety contains from 6 to 18 carbon atoms and in which the average carbon chain length of the composition is from about 9 to about 14 comprising a mixture of two or more at least binary components of alkylpolyglycosides in which one of the binary components has a lower average alkyl chain length than the other binary components and wherein the binary component having the lower average alkyl chain length and each other binary component is present in the mixture in relation to its average alkyl chain length in an amount effective to provide the surfactant composition with the average alkyl chain of about 9 to about 14 and a hydrophilic lipophilic balance (HLB) in the range of about 10 to about 16, and wherein at least one or all of the binary components comprise a Flory distribution of polyglycosides derived from the acid-catalyzed reaction of an alcohol containing from 6–20 carbon atoms and a suitable saccharide from which excess alcohol has been separated, and wherein the binary component having the lower average alkyl chain length is present in a weight ratio to the other binary components in the range of about 1.25:1 to about 10:1.

17. An alkylpolyglycoside surfactant composition as defined in claim 16 in which said average carbon chain length of the composition is above about 9 up to about 12.

18. An alkylpolyglycoside surfactant composition as defined in claim 16 in which the HLB is in the range of about 11 to about 14.

19. An alkylpolyglycoside surfactant composition as defined in claim 16 in which said average carbon chain length of the composition is above about 9 and below about 12, and one of the binary components of alkylpolyglycosides is a mixture of a $C_8$ alkylpolyglycoside and a $C_{10}$ alkylpolyglycoside.

20. An alkylpolyglycoside surfactant composition as defined in claim 16 in which said average carbon chain length of the composition is above about 9 and below about 12, and one of the binary components of alkylpolyglycosides is a mixture of a $C_{12}$ alkylpolyglycoside, a $C_{14}$ alkylpolyglycoside and a $C_{16}$ alkylpolyglycoside.

21. An alkylpolyglycoside surfactant composition as defined in claim 20 in which a second binary component of alkylpolyglycosides is a mixture of a $C_8$ alkylpolyglycoside and a $C_{10}$ alkylpolyglycoside.

22. An alkylpolyglycoside surfactant composition as defined in claim 21 in which the ratio by weight of the mixture of $C_8$ and $C_{10}$ alkylpolyglycosides to the mixture of the $C_{12}$, $C_{14}$ and $C_{16}$ alkylpolyglycosides is above about a 1.25:1 to about 9:1.

23. The composition as defined in claim 22 in which said ratio is about 1.5:1 to about 4:1.

24. The composition as defined in claim 22 in which said ratio is about 1.7:1, said mixture of $C_8$ and $C_{10}$ alkylpolyglycosides is comprised by weight of about 45% $C_8$ and about 55% $C_{10}$ and said mixture of $C_{12}$, $C_{14}$ and $C_{16}$ alkylpolyglycosides is comprised by weight of about 68% $C_{12}$, about 26% $C_{14}$ and about 6% $C_{16}$.

25. The composition as defined in claim 24, wherein the composition has an HLB of about 13 and an average degree of polymerization of about 1.4 to about 2.5.

26. The composition as defined in claim 25, in which said average degree of polymerization is about 1.6.

27. A surfactant composition selected from the group consisting of a hard surface cleaner, a soil cleaning composition, a laundry detergent, and a personal care composition selected from the group consisting of a shampoo, a soap, a lotion, a cream, a facial cleanser, a foam bath composition, a toothpaste, a mouthwash and an antiperspirant, containing the alkyl polyglycoside surfactant composition of claim 16, and at least one adjuvant selected from the group consisting of a co-surfactant, a detergency builder, a soil suspending agent, a brightening agent, an abrasive, a dye, a fragrance, a fabric conditioning agent, a hair conditioning agent, a hydrotrope, a solvent, a filler, an antimicrobial agent, and a preservative.

28. The surfactant composition as defined in claim 27 wherein the composition is a hard surface cleaner and further comprises an anionic surfactant.

29. The hard surface cleaner as defined in claim 28 in which the alkylpolyglycoside surfactant composition has an average carbon chain length above about 9 and below about 12, and one of the binary components of alkyl polyglycosides is a mixture of a $C_{12}$ alkylpolyglycoside, a $C_{14}$ alkylpolyglycoside, and a $C_{16}$ alkylpolyglycoside and the second binary component of alkyl polyglycosides is a mixture of a $C_8$ alkylpolyglycoside and a $C_{10}$ alkylpolyglycoside, wherein the ratio by weight of the mixture of $C_8$ and $C_{10}$ alkylpolyglycoside to the mixture of the $C_{12}$, $C_{14}$, and $C_{16}$ alkyl polyglycosides is above 1.25:1 to about 9:1.

30. The hard surface cleaner as defined in claim 29 in which the ratio by weight of the mixture of $C_8$ and $C_{10}$ alkylpolyglycosides to the mixture of $C_{12}$, $C_{14}$ and $C_{16}$ alkylpolyglycosides is about 1.5:1 to about 4:1.

31. The hard surface cleaner as defined in claim 30 in which said ratio is about 2:1.

32. The hard surface cleaner as defined in claim 31 and further comprising tetrapotassium pyrophosphate, sodium metasilicate pentahydrate, sodium hydroxide and sodium xylene sulfonate.

33. The hard surface cleaner as defined in claim 31 wherein said cleaner is an aluminum cleaner.

34. The hard surface cleaner as defined in claim 33 and further comprising sodium EDTA, sodium gluconate, sodium silicate and potassium hydroxide.

35. A surfactant composition containing the alkylpolyglycoside composition defined in claim 27 wherein the composition is a soil cleaning composition.

36. A soil cleaning composition as defined in claim 35 in which the alkylpolyglycoside surfactant composition has an average carbon chain length above about 9 and below about 12, and one of the binary components of alkyl polyglycosides is a mixture of a $C_{12}$ alkylpolyglycoside, a $C_{14}$ alkylpolyglycoside, and a $C_{16}$ alkylpolyglycoside and the second binary component of alkyl polyglycosides is a mixture of a $C_8$ alkylpolyglycoside and a $C_{10}$ alkylpolyglycoside, wherein the ratio by weight of the mixture of $C_8$ and $C_{10}$ alkylpolyglycoside to the mixture of the $C_{12}$, $C_{14}$, and $C_{16}$ alkyl polyglycosides is above 1.25:1 to about 9:1.

37. The soil cleaning composition as defined in claim 36 in which the ratio by weight of the mixture of $C_8$ and $C_{10}$ alkylpolyglycosides to the mixture of $C_{12}$, $C_{14}$ and $C_{16}$ alkylpolyglycosides is about 2:1 to about 3:1.

38. A personal care composition containing the surfactant composition defined in claim 27 in which the alkylpolyglycoside surfactant composition has an average carbon chain length above about 9 and below about 12, and one of the binary components of alkyl polyglycosides is a mixture of a $C_{12}$ alkylpolyglycoside, a $C_{14}$ alkylpolyglycoside, and a $C_{16}$ alkylpolyglycoside and the second binary component of alkyl polyglycosides is a mixture of a $C_8$ alkylpolyglycoside and a $C_{10}$ alkylpolyglycoside, wherein the ratio by weight of the mixture of $C_8$ and $C_{10}$ alkylpolyglycoside to the mixture of the $C_{12}$, $C_{14}$, and $C_{16}$ alkyl polyglycosides is above 1.25:1 to about 9:1.

39. The personal care composition as defined in claim 38 in which the ratio by weight of the mixture of $C_8$ and $C_{10}$ alkylpolyglycosides to the mixture of $C_{12}$, $C_{14}$ and $C_{16}$ alkylpolyglycosides is about 1.5:1 to about 2:1.

40. The personal care composition as defined in claim 39 wherein the personal care composition is a shampoo.

41. The personal care shampoo composition as defined in claim 40 and further containing an anionic co-surfactant.

42. The personal care shampoo as defined in claim 41 in which said anionic co-surfactant is an ethoxylated or unethoxylated alkyl sulfate in which the alkyl group has from about 10 to about 18 carbon atoms.

43. The personal care shampoo as defined in claim 42 wherein said anionic co-surfactant is sodium or ammonium laureth sulfate.

44. The personal care composition as defined in claim 38 wherein the personal care composition is a liquid soap for application to human skin.

45. The personal care liquid soap as defined in claim 44 and further containing an anionic co-surfactant.

46. The personal care liquid soap as defined in claim 45 and further containing an antimicrobial agent.

47. The personal care liquid soap as defined in claim 45 wherein said anionic co-surfactant is sodium lauryl sulfate.

48. The personal care composition as defined in claim 38 wherein the personal care composition is a facial cleanser.

49. The personal care facial cleanser as defined in claim 48 and further containing an anionic co-surfactant.

50. The personal care facial cleanser as defined in claim 49 in which said anionic co-surfactant is disodium laureth sulfosuccinate.

51. The personal care composition as defined in claim 38 wherein the personal care composition is a foam bath composition.

52. The personal care foam bath composition as defined in claim 51 and further containing an anionic co-surfactant.

53. The personal care foam bath composition as defined in claim 52 in which said anionic co-surfactant is sodium laureth sulfate.

54. The personal care composition as defined in claim 38 wherein the personal care composition is a toothpaste.

55. The personal care composition as defined in claim 38 wherein the personal care composition is a mouthwash.

56. The personal care composition as defined in claim 38 wherein the personal care composition is an antiperspirant.

57. The personal care composition as defined in claim 38 wherein the personal care composition is a bar of soap.

58. The personal care bar of soap as defined in claim 57 and further containing an acyl isethionate co-surfactant.

59. A laundry detergent containing the surfactant composition of claim 16.

60. A personal care composition containing the surfactant composition of claim 16.

61. The personal care composition as defined in claim 60 wherein the personal care composition is a shampoo.

62. The personal care composition as defined in claim 60 wherein the personal care composition is a soap.

63. The personal care composition as defined in claim 60 wherein the personal care composition is a lotion.

64. The personal care composition as defined in claim 60 wherein the personal care composition is a cream.

65. The method of preparing a personal care composition comprising adding to said personal care composition a surfactant effective amount of the alkylpolyglycoside surfactant defined in claim 16.

66. The method as defined in claim 65 wherein said personal care composition is selected from the group consisting of a shampoo, a soap, a facial cleanser, a foam bath, a toothpaste, a mouthwash and an antiperspirant composition.

67. A method of preparing a cleaning composition comprising adding to said cleaning composition a surfactant effective amount of the alkylpolyglycoside surfactant defined in claim 16.

68. The method as defined in claim 67 wherein said cleaning composition is a hard surface cleaner or a laundry detergent composition.

69. An alkylpolyglycoside surfactant composition having an hydrophilic lipophilic balance (HLB) in the range of about 10 to about 16, an average degree of polymerization of about 1.4 to about 2 and an average carbon chain length of the composition above about 9 and below about 12 comprising a mixture of (a) a binary component comprised of a mixture of a $C_8$ alkylpolyglycoside, and a $C_{10}$ alkylpolyglycoside; and (b) a second component comprised of a mixture of a $C_{12}$ alkylpolyglycoside, a $C_{14}$ alkylpolyglycoside and a $C_{16}$ alkylpolyglycoside, in which mixture the ratio by weight of binary component (a) to component (b) is about 1.5:1 to about 4:1, and wherein at least one or both components are present in a substantially Flory distribution of polyglycosides and contain less than about 5% by weight alcohol.

70. The alkylpolyglycoside surfactant composition as defined in claim 69, wherein the HLB is in the range of about 11 to about 14, the average DP is about 1.6, the $C_8$ and $C_{10}$ binary component (a) is comprised by weight of about 45% $C_8$ and about 55% $C_{10}$ and the $C_{12}$, $C_{14}$ and $C_{16}$ component (b) is comprised of about 68% $C_{12}$, about 26% $C_{14}$ and about 6% $C_{16}$ and the ratio by weight of component (a) to component (b) is about 1.7 whereby the $C_{10}$ species present in the composition predominates by weight.

* * * * *